(12) United States Patent
Zhang

(10) Patent No.: US 11,836,916 B2
(45) Date of Patent: Dec. 5, 2023

(54) DETECTING VASCULAR CALCIFICATION

(71) Applicant: Neusoft Medical Systems Co., Ltd., Liaoning (CN)

(72) Inventor: Congrong Zhang, Liaoning (CN)

(73) Assignee: Neusoft Medical Systems Co., Ltd., Shenyang (CN)

( * ) Notice: Subject to any disclaimer, the term of this patent is extended or adjusted under 35 U.S.C. 154(b) by 296 days.

(21) Appl. No.: 17/220,884

(22) Filed: Apr. 1, 2021

(65) Prior Publication Data

US 2021/0319553 A1 Oct. 14, 2021

(30) Foreign Application Priority Data

Apr. 8, 2020 (CN) .......................... 202010271173.2

(51) Int. Cl.
*G06T 7/00* (2017.01)
*G06N 3/04* (2023.01)
(Continued)

(52) U.S. Cl.
CPC ............ *G06T 7/0012* (2013.01); *A61B 6/032* (2013.01); *A61B 6/486* (2013.01); *A61B 6/503* (2013.01);
(Continued)

(58) Field of Classification Search
CPC ......... G06T 7/0012; G06T 7/136; G06T 7/11; G06T 2200/04; G06T 2207/10081;
(Continued)

(56) References Cited

U.S. PATENT DOCUMENTS

2003/0165262 A1* 9/2003 Nishikawa ............ G06T 7/0012
382/128
2003/0176780 A1* 9/2003 Arnold ...................... G06T 7/62
600/407
(Continued)

FOREIGN PATENT DOCUMENTS

CN 106447645 A 2/2017
CN 108171698 A 6/2018
(Continued)

OTHER PUBLICATIONS

Cai et al, "Abdominal Aorta Calcification Score Can Be Used to Estimate the Calcification Degree of Coronary Artery in Hemodialysis Patients," Chin. J. Blood Purif. Apr. 2013, (12)4: 189-194 (with English abstract).
Guo et al, "Aortic Calcification Detection in CT Images," Journal of Qingdao University (Natural Science Edition), Feb. 2013, 26(1):50-54 (with English abstract).
(Continued)

*Primary Examiner* — Shefali D Goradia
(74) *Attorney, Agent, or Firm* — Fish & Richardson P.C.

(57) ABSTRACT

Methods, systems, devices and apparatus for vascular calcification detection are provided. In one aspect, a vascular calcification detection method includes: obtaining a three-dimensional non-angiographic image, obtaining one or more to-be-detected sub-regions included in each of at least two to-be-detected regions in the three-dimensional non-angiographic image by inputting the three-dimensional non-angiographic image into a pre-trained region identification network, the to-be-detected regions including an aortic region and a coronary region; for each of the to-be-detected regions, obtaining a calcification region in the to-be-detected region by threshold segmentation; based on the calcification region and the one or more to-be-detected sub-regions included in the to-be-detected region, determining a corre-
(Continued)

sponding calcification sub-region in each of the one or more to-be-detected sub-regions; and displaying the corresponding calcification sub-region in each of the one or more to-be-detected sub-regions in the three-dimensional non-angiographic image.

20 Claims, 3 Drawing Sheets

(51) Int. Cl.
*G06T 7/136* (2017.01)
*G06T 7/11* (2017.01)
*A61B 6/03* (2006.01)
*A61B 6/00* (2006.01)
*G06N 3/08* (2023.01)

(52) U.S. Cl.
CPC ............ *A61B 6/5217* (2013.01); *G06N 3/04* (2013.01); *G06N 3/08* (2013.01); *G06T 7/11* (2017.01); *G06T 7/136* (2017.01); *G06T 2200/04* (2013.01); *G06T 2207/10081* (2013.01); *G06T 2207/20084* (2013.01); *G06T 2207/30048* (2013.01); *G06T 2207/30101* (2013.01)

(58) Field of Classification Search
CPC .......... G06T 2207/20084; G06T 2207/30048; G06T 2207/30101; A61B 6/032; A61B 6/486; A61B 6/503; A61B 6/5217; G06N 3/04; G06N 3/08
See application file for complete search history.

(56) References Cited

U.S. PATENT DOCUMENTS

2008/0279435 A1* 11/2008 Arnold ................. G06T 7/0012
382/131
2011/0164035 A1* 7/2011 Liao ....................... A61B 6/487
345/419

FOREIGN PATENT DOCUMENTS

| CN | 109288536 A | * | 2/2019 |
| CN | 109389592 A | | 2/2019 |
| EP | 3361445 A1 | | 8/2018 |

OTHER PUBLICATIONS

Kang et al, "Coronary Vessel Segmentation Method Based on Deep Convolutional Network," Electronic Technology & Software Engineering, Mar. 2020, 2020(6):140-144 (with English abstract).
Office Action and Search Report in Chinese Appln. No. 202010271173.2, dated Sep. 28, 2022, 18 pages (with Machine Translation).
Lu et al., "Correlation Analysis of Coronary Artery Calcification, Aortic Calcification and Cardiovascular Diseases", Guide of China Medicine, Jan. 2016, 3 pages (submitted with machine abstract translation).
Modern Endocrinology, Yu (ed)., Jan. 2013, pp. 268-274, 19 pages (submitted with machine translation).
Office Action and Search Report in Chinese Appln. No. 202010271173.2, dated Mar. 22, 2023, 18 pages (submitted with machine translation).
Office Action in Chinese Appln. No. 2020102711732, dated Aug. 1, 2023, 20 pages (With Machine Translation).

* cited by examiner

DETECTING VASCULAR CALCIFICATION

CROSS REFERENCE TO RELATED APPLICATIONS

This application claims priority to Chinese Patent Application No. 202010271173.2 entitled "VASCULAR CALCIFICATION DETECTION METHOD AND APPARATUS" filed on Apr. 8, 2020, the entire content of which is incorporated herein by reference.

TECHNICAL FIELD

The present disclosure relates to the field of medical imaging and in particular to vascular calcification detection.

BACKGROUND

Along with aging of population, cardiovascular disease such as coronary heart disease has become a frequent disease for the elder persons. Relevant researches show that aortic calcification and coronary calcification are both correlated with incidence of coronary heart disease and therefore have become important prediction indicators for incidence of coronary heart disease.

SUMMARY

Implementations of the present disclosure provide methods, devices, systems and apparatus for detecting vascular calcification.

In general, one innovative aspect of the subject matter described in this specification can be embodied in methods that include the actions of detecting vascular calcification to obtain a more accurate and more comprehensive vascular calcification detection result, including: obtaining a three-dimensional non-angiographic image; obtaining one or more to-be-detected sub-regions included in each of at least two to-be-detected regions in the three-dimensional non-angiographic image by inputting the three-dimensional non-angiographic image into a pre-trained region identification network, the at least two to-be-detected regions including an aortic region and a coronary region; for each of the at least two to-be-detected regions, obtaining a calcification region in the to-be-detected region by threshold segmentation; determining, based on the calcification region and the one or more to-be-detected sub-regions included in the to-be-detected region, a corresponding calcification sub-region in each of the one or more to-be-detected sub-regions included in the to-be-detected region; and displaying, in the three-dimensional non-angiographic image, the corresponding calcification sub-region in each of the one or more to-be-detected sub-regions.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination.

In some embodiments, the region identification network is pre-trained by: for each of at least one sample image that includes a three-dimensional non-angiographic image involving the coronary region or the aortic region, obtaining one or more predicted sub-regions of the sample image from the region identification network by inputting the sample image into the region identification network; and adjusting a network parameter of the region identification network according to a difference between the obtained one or more predicted sub-regions and one or more corresponding actual sub-regions in the sample image.

In some embodiments, obtaining the calcification region in the to-be-detected region by the threshold segmentation includes: marking a region with a CT value greater than or equal to a preset threshold within the aortic region in the to-be-detected region as a suspicious aortic calcification region; and obtaining an aortic calcification region by removing a non-calcification region within the suspicious aortic calcification region according to a first preset condition. The first preset condition can include preset regional connectivity and regional volume.

In some embodiments, obtaining the calcification region in the to-be-detected region by the threshold segmentation includes: marking a region with a CT value greater than or equal to a preset threshold within the coronary region in the to-be-detected region as a suspicious coronary calcification region; and obtaining a coronary calcification region by removing a non-calcification region within the suspicious coronary calcification region according to a second preset condition. The second preset condition can include preset regional morphology and regional space feature.

In some embodiments, after displaying the calcification sub-region, the method further includes: receiving a parameter modification request, wherein the parameter modification request comprises data for updating the calcification sub-region; and updating the corresponding calcification sub-region according to the parameter modification request.

In some embodiments, after displaying the calcification sub-region, the method further includes: calculating a score value of the corresponding calcification sub-region, wherein the score value represents a calcification degree of the corresponding calcification sub-region; and displaying the score value of the corresponding calcification sub-region.

The exemplary embodiments will be described in detail here, and examples thereof are illustrated in the accompanying drawings. When the following description refers to the accompanying drawings, unless otherwise stated, the same reference signs in different drawings designate the same or similar elements. The implementation manners described in the following exemplary embodiments do not represent all implementation manners consistent with the present application. On the contrary, they are merely examples of devices and methods consistent with some aspects of the present application as defined in the appended claims.

DETAILED DESCRIPTION

Aortic calcification (including aortic valve calcification, ascending aorta calcification, aortic arch calcification, and descending aorta calcification) and coronary calcification (including left main coronary artery calcification, left anterior descending artery calcification, circumflex artery calcification, right coronary artery calcification) are both correlated with incidence of coronary heart disease and are important prediction indicators for incidence of coronary heart disease. The existing vascular calcification detection method mainly focuses on detection analysis of coronary calcification circumstances and performs calcification region extraction based on a coronary extraction result. However, if there exists inaccurate coronary segmentation, the method may produce an inaccurate calcification detection result.

Implementations of the present disclosure provide a method of detecting vascular calcification, which can address the above calcification detection problem. In this method, one or more to-be-detected sub-regions included in each of at least two to-be-detected regions in a three-dimensional non-angiographic image is obtained by use of a pre-trained region identification network. Then for each of the to-be-detected regions, a calcification region in the to-be-detected region is obtained by a threshold segmentation method. The calcification region is determined as a calcification sub-region in each of the one or more to-be-detected sub-regions included in the to-be-detected region based on the one or more to-be-detected sub-regions included in the to-be-detected region. Finally the calcification sub-region in each of the one or more to-be-detected sub-regions is displayed. In this detection method, regions in a three-dimensional non-angiographic image are classified by a neural network and a calcification region is obtained by a threshold segmentation method, thereby improving the segmentation accuracy and increasing the accuracy of vascular calcification detection. Further, this detection method does not perform calcification region extraction any more by only relying on a coronary extraction result but perform calcification detection for both a coronary region and an aortic region, thereby producing a more accurate and more comprehensive vascular calcification detection result which provides an important basis for clinically predicting the risk of coronary heart disease.

To illustrate the method of detecting vascular calcification in the present disclosure, the implementation process of the technical solution in the present disclosure will be detailed below in combination with the accompanying drawings and specific examples.

Figure 1:
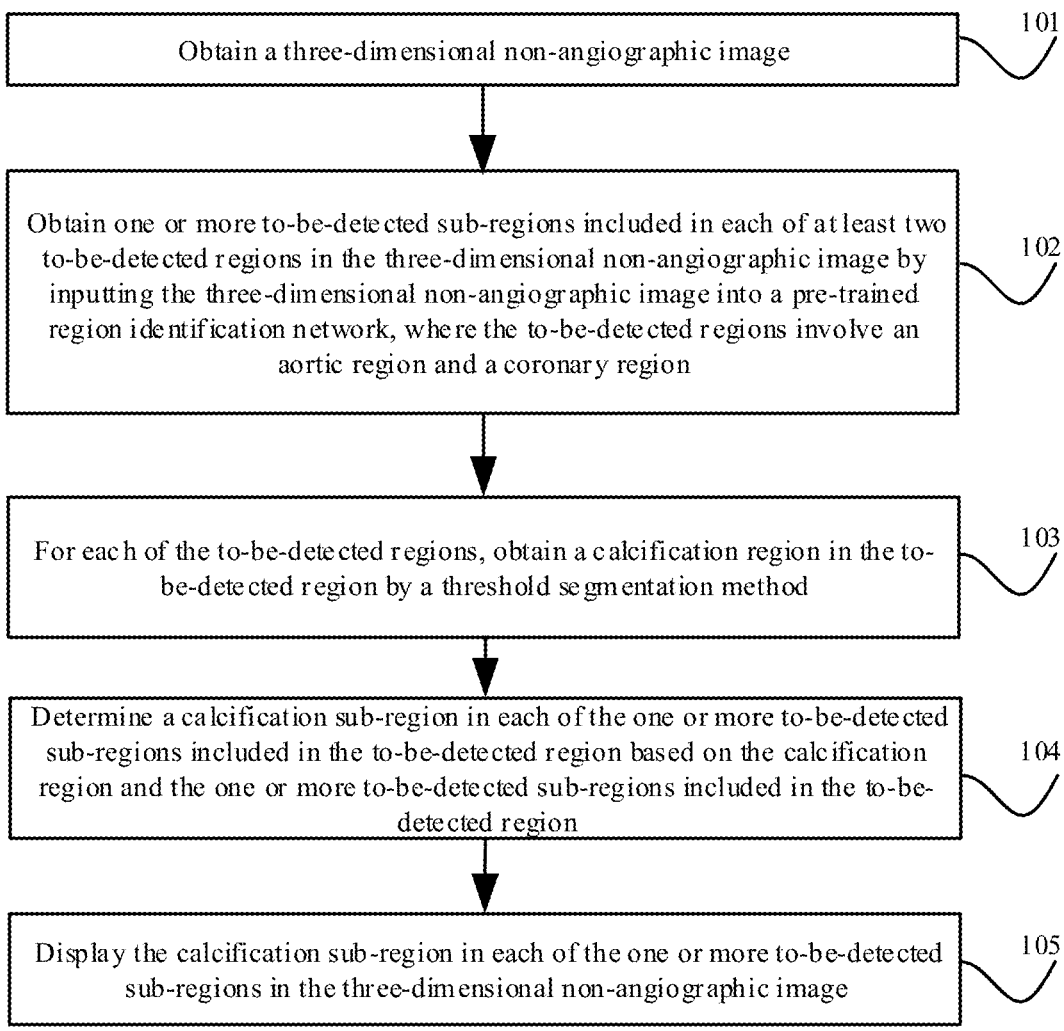
FIG. 1 is a flowchart of a method of detecting vascular calcification according to one or more embodiments of the present disclosure.

FIG. 1 is a flowchart of a process of a method of detecting vascular calcification according to one or more embodiments of the present disclosure. As shown in FIG. 1, the process may include steps 101-105.

At step 101, a three-dimensional non-angiographic image is obtained.

A three-dimensional non-angiographic image to be subjected to calcification detection is obtained. The three-dimensional non-angiographic image may be a three-dimensional image reconstructed after CT scan is performed for a sick body, and the three-dimensional non-angiographic image can be a non-angiographic image obtained by performing CT scan for a sick body without contrast medium. For example, the three-dimensional non-angiographic image may be a three-dimensional medical chest and abdomen non-angiographic image.

At step 102, one or more to-be-detected sub-regions included in each of at least two to-be-detected regions in the three-dimensional non-angiographic image is obtained by inputting the three-dimensional non-angiographic image into a pre-trained region identification network, where the to-be-detected regions involve an aortic region and a coronary region.

Figures 3A, 3B, 3C:
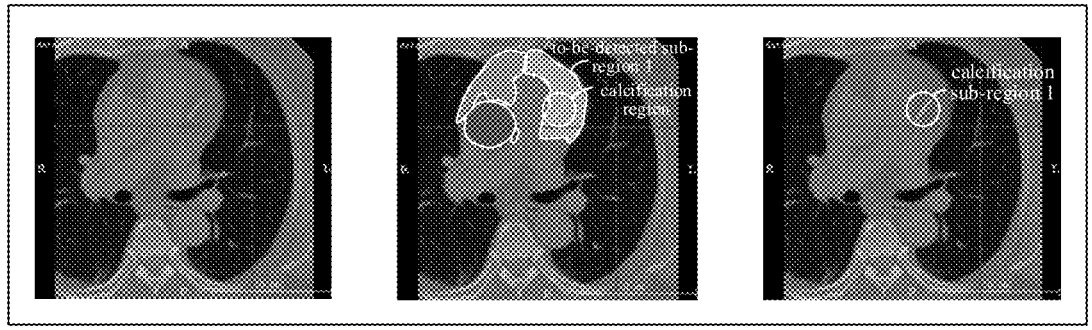
FIG. 3a is a schematic diagram of a three-dimensional non-angiographic image according to one or more embodiments of the present disclosure.
FIG. 3b is a schematic diagram of a to-be-detected sub-region according to one or more embodiments of the present disclosure.
FIG. 3c is a schematic diagram of a calcification sub-region according to one or more embodiments of the present disclosure.

In this step, the three-dimensional non-angiographic image is input into the pre-trained region identification network, and then at least two to-be-detected regions in the non-angiographic image and the one or more to-be-detected sub-regions included in each of the at least two to-be-detected regions are identified through the region identification network, where the to-be-detected regions may involve the aortic region and the coronary region. Illustratively, FIG. 3a shows a three-dimensional non-angiographic image according to one or more embodiments of the present disclosure. The region identification network identifies a plurality of to-be-detected sub-regions, for example, a to-be-detected sub-region 1 shown in FIG. 3b from the three-dimensional non-angiographic image of FIG. 3a. Descriptions are made with an input three-dimensional medical chest and abdomen non-angiographic image as an example. The pre-trained region identification network identifies the aortic region and the coronary region involved in the to-be-detected regions. Further, the region identification network can identify to-be-detected sub-regions included in the aortic region: an aortic valve region, an ascending aorta region, a aortic arch region, and a descending aorta region; the region identification network can identify to-be-detected sub-regions included in the coronary region: a left main coronary artery region, a left anterior descending artery region, a circumflex artery region, and a right coronary artery region. The region identification network in this step may be obtained by pre-training a deep neural network, which will be described in details subsequently.

At step 103, for each of the to-be-detected regions, a calcification region in the to-be-detected region is obtained by a threshold segmentation method.

After a to-be-detected region in the three-dimensional non-angiographic image is identified through the region identification network, calcification regions in the to-be-detected region are obtained by the threshold segmentation method, including obtaining a calcification region in the aortic region, a calcification region in the coronary region, and/or calcification regions in different to-be-detected sub-regions and so on. A region with a CT value greater than or equal to (or no smaller than) a preset threshold in the to-be-detected region may be marked as a calcification region. In some embodiments, a region with a CT value greater than or equal to a preset threshold in the aortic region may be marked as a calcification region. In some embodiments, a region with a CT value greater than or equal to a preset threshold in the coronary region may be marked as a calcification region. In some embodiments, a region with a CT value greater than or equal to a preset threshold in a to-be-detected sub-region of the to-be-detected region may be marked as a calcification region. Illustratively, as shown in FIG. 3b, a region with a CT value greater than or equal to a preset threshold in the to-be-detected sub-region 1 is marked as a calcification region.

In an example, obtaining the calcification region in the to-be-detected region by the threshold segmentation method includes: marking a region with a CT value greater than or equal to a preset threshold within the aortic region in the to-be-detected region as a suspicious aortic calcification region; obtaining an aortic calcification region by removing a non-calcification region within the suspicious aortic calcification region according to a first preset condition. In some cases, the non-calcification region does not satisfy the first preset condition, while the aortic calcification region satisfies the first preset condition. In some examples, the first preset condition includes a preset regional connectivity and regional volume. If a region has a volume no less than the preset regional connectivity and regional volume, it can be determined that the region satisfies the first preset condition. If a region has a volume less than the preset regional connectivity and regional volume, it can be determined that the region does not satisfy the first preset condition.

The above example shows the detailed steps of obtaining the calcification region from the aortic region in the to-be-detected region. Descriptions are made with the three-dimensional medical chest and abdomen non-angiographic image as an example. A region with a CT value greater than or equal to a preset threshold (e.g., 130) within an aortic region in a to-be-detected region is marked as a suspicious aortic calcification region. An aortic calcification region can be obtained by removing a non-calcification region within the suspicious aortic calcification region according to the preset condition. The non-calcification region does not satisfy the preset condition of the regional connectivity and regional volume. The preset condition of regional connectivity and regional volume may be set according to conventional experiences. For example, a region with a volume less than a fixed value in the suspicious aortic calcification region may be classified as a non-calcification region and removed.

In the above example, with the aortic region as a calcification detection object, detection is performed for the calcification region in the aortic region, and the non-calcification region is further removed according to the preset condition for the aortic region, so that the calcification region in the aortic region is more accurately identified, thereby producing a more accurate and more comprehensive vascular calcification detection result which provides an important basis for clinically predicting the risk of coronary heart disease.

In an example, obtaining the calcification region in the to-be-detected region by the threshold segmentation method includes: marking a region with a CT value greater than or equal to a preset threshold within the coronary region in the to-be-detected region as a suspicious coronary calcification region; obtaining a coronary calcification region by removing a non-calcification region within the suspicious coronary calcification region according to a second preset condition. In some cases, the non-calcification region does not satisfy the second preset condition, while the coronary calcification region satisfies the second preset condition. In some examples, the second preset condition includes preset regional morphology and regional space feature. If a region has a regional morphology and regional space feature matching the preset regional morphology and regional space feature, it can be determined that the region satisfies the second preset condition. If a region has a regional morphology and regional space feature not matching the preset regional morphology and regional space feature, it can be determined that the region does not satisfy the second preset condition.

The above example shows the detailed steps of obtaining the calcification region from the coronary region in the to-be-detected region. Descriptions are made with the three-dimensional medical chest and abdomen non-angiographic image as an example. A region with a CT value greater than or equal to a preset threshold (e.g., 130) within a coronary region in a to-be-detected region is marked as a suspicious coronary calcification region. A coronary calcification region can be obtained by removing a non-calcification region within the suspicious coronary calcification region according to the preset condition. The non-calcification region does not satisfy the preset condition of the regional morphology and regional space feature. The preset condition of regional morphology and regional space feature may be set according to conventional experiences. For example, a region with an area unsatisfying the preset condition in the suspicious coronary calcification region may be classified as a non-calcification region and removed.

In the above example, with the coronary region as a calcification detection object, detection is performed for the calcification region in the coronary region, and the non-calcification region is further removed according to the preset condition for the coronary region, so that the calcification region in the coronary region is more accurately identified, thereby producing a more accurate and more comprehensive vascular calcification detection result which provides an important basis for clinically predicting the risk of coronary heart disease.

At step 104, a calcification sub-region in each of the one or more to-be-detected sub-regions included in the to-be-detected region is determined based on the calcification region and the one or more to-be-detected sub-regions included in the to-be-detected region.

A to-be-detected region may include a plurality of to-be-detected sub-regions, and a calcification region in each of the plurality of to-be-detected sub-regions is determined as a corresponding calcification sub-region. The corresponding calcification sub-regions in the plurality of to-be-detected sub-regions of the to-be-detected region form the calcification region in the to-be-detected region. In some examples, the aortic region in the to-be-detected region may include a plurality of to-be-detected sub-regions: an aortic valve region, an ascending aorta region, an aortic arch region, and a descending aorta region. Corresponding calcification sub-regions in these to-be-detected sub-regions can be determined as: an aortic valve calcification sub-region, an ascending aorta calcification sub-region, an aortic arch calcification sub-region, and a descending aorta calcification sub-region. In some examples, the coronary region in the to-be-detected region may include a plurality of to-be-detected sub-regions: a left main coronary artery region, a left anterior descending artery region, a circumflex artery region, and a right coronary artery region. Corresponding calcification sub-regions in these to-be-detected sub-regions can be determined as: a left main coronary artery calcification sub-region, a left anterior descending artery calcification sub-region, a circumflex artery calcification sub-region, and a right coronary artery calcification sub-region. Illustratively, as shown in FIG. 3c, a calcification region corresponding to the to-be-detected sub-region 1 in FIG. 3b is determined as a calcification sub-region 1.

At step 105, the calcification sub-region in each of the one or more to-be-detected sub-regions is displayed in the three-dimensional non-angiographic image.

In the three-dimensional non-angiographic image, each detected calcification sub-region is displayed in an easy-to-view manner. For example, the calcification sub-region is displayed in color in a 2D image or displayed in a 3D image in color or in transparent drawing manner. Further, different calcification sub-regions may be distinguished from each other by using different colors, or corresponding marking is performed for each calcification sub-region to distinguish different calcification sub-regions. In addition, a calcification score, a plaque length and the like of a calcification sub-region in the aortic region may be displayed in a graph or an image window; a calcification score of a calcification sub-region in the coronary region (e.g., calcification Agatston score, calcification volume score, and calcification quality score, and the like) may be displayed in a graph or an image window. In this case, a user may easily view them.

In an example, after the calcification sub-region is displayed, the method can further includes: receiving a parameter modification request, where the parameter modification request includes data for updating the calcification sub-region; and updating the calcification sub-region according to the parameter modification request.

In the above example, after the calcification sub-region is displayed in the three-dimensional non-angiographic image, if a parameter modification request is received, a corresponding calcification sub-region is updated according to data included in the parameter modification request. For example, if a user thinks a scope of one calcification sub-region is obviously unreasonable after obtaining a vascular calcification detection result, the user may manually adjust the scope of the calcification sub-region according to the experiences of the user, so as to make the calcification detection result more accurate. For another example, the user may distinguish different calcification sub-regions by using different colors after obtaining a calcification detection result. If the user finds that the color representation of one calcification sub-region is obviously wrong, the user may advertise an instruction to modify color data corresponding to the calcification sub-region, so as to make the color representation type more accurate.

In the method of detecting vascular calcification of this example, one or more to-be-detected sub-regions included in each of at least two to-be-detected regions in a three-dimensional non-angiographic image is identified by use of a pre-trained region identification network, and then for each of the to-be-detected regions, a calcification region in the to-be-detected region is obtained by a threshold segmentation method, and the calcification region is determined as a calcification sub-region in each of the one or more to-be-detected sub-regions included in the to-be-detected region based on the one or more to-be-detected sub-regions included in the to-be-detected region, finally the calcification sub-region in each of the one or more to-be-detected sub-regions is displayed. In this detection method, regions in a three-dimensional non-angiographic image are classified by a neural network and a calcification region is obtained by a threshold segmentation method, thereby improving the segmentation accuracy and increasing the accuracy of vascular calcification detection. Further, this detection method does not perform calcification region extraction any more by only relying on a coronary extraction result but perform calcification detection for both a coronary region and an aortic region, thereby producing a more accurate and more comprehensive vascular calcification detection result which provides an important basis for clinically predicting the risk of coronary heart disease.

In another example, after the calcification sub-region is displayed, the method further includes: calculating a score value of the calcification sub-region, wherein the score value represents a calcification degree of the calcification sub-region; and displaying the score value, e.g., in the three-dimensional non-angiographic image. That is, after each calcification region and each calcification sub-region are detected by the above vascular calcification detection method, calculation of the calcification score value corresponding to each calcification sub-region is further included.

When the calcification score of each calcification sub-region in the aortic region is calculated, the following calculation method may be used: a volume score method and a Kauppila semi-quantitative score method. The calcification score is calculated by the volume score method based on the following principle: the number of pixel points in the calcification region is multiplied by a physical unit of the pixel point (for example, the physical unit is $mm^3$). For example, for each calcification sub-region in the aortic region, the number of pixel points included in the calcification sub-region is calculated and then multiplied by the physical unit of the pixel point, so as to obtain the calcification volume score of the calcification sub-region. A partial calcification volume score of the aortic region may be obtained by calculating a sum of calcification volume scores of part of calcification sub-regions in the aortic region. A total calcification volume score of the entire aortic region may be obtained by calculating a sum of calcification volume scores of all calcification sub-regions in the aortic region.

In addition, a calcification degree of the aortic region may be evaluated by calculating the calcification score of each calcification sub-region in the aortic region by a semi-quantitative score method, for example, by the Kauppila semi-quantitative score method. The specific calculation process can be shown as follows: a plaque length of each calcification sub-region in the aortic region is firstly calculated, each calcification sub-region in the aortic region is projected onto a plane to calculate a projection length which is taken as the plaque length of the calcification sub-region; then, the calcification degree of each calcification sub-region is scored according to a ratio M of the plaque length of each calcification sub-region in the aortic region to a respective artery wall length, where the scoring may be performed by referring to, for example, the following scoring standard: the calcification score of no calcification is 0 score; the calcification score of mild calcification ($M<1/3$) is 1 score; the calcification score of moderate calcification ($1/3<M<2/3$) is 2 scores; and the calcification score of heavy calcification ($M>2/3$) is 3 scores. A total calcification score of the calcification sub-regions corresponding to each of the aortic valve region, the ascending aorta region, the aortic arch region, and the descending aorta region in the aortic region may be calculated. For example, the calcification score of an aortic valve calcification sub-region may be obtained by accumulating the calcification scores of all calcification sub-regions corresponding to the aortic valve region. Further, the calcification degree of each type of aortic calcification sub-region may be evaluated to be mild calcification, moderate calcification or heavy calcification according to the calcification score of the aortic valve calcification sub-region, the calcification score of an ascending aorta calcification sub-region, the calcification score of an aortic arch calcification sub-region, and the calcification score of a descending aorta calcification sub-region respectively. Alternatively, the calcification degree of the entire aortic region may be evaluated by obtaining the total calcification score of the entire aortic region through calculation of the calcification scores of all calcification sub-regions in the aortic region.

In an example, displaying the score value may include: displaying respective calcification scores of various calcification sub-regions in the aortic region. In an example, displaying the score value may include: displaying respective plaque lengths of various calcification sub-regions in the aortic region.

When the calcification score of each calcification sub-region in the coronary region is calculated, the following calculation method may be used: an Agatston score method, a volume score method, and a quality score method. The calcification score is calculated by the Agatston score method based on the following principle: calcification density score×calcification area. Specifically, for each calcification sub-region in the coronary region, the calcification density score of the calcification sub-region is firstly obtained according to the CT value of the calcification sub-region. For example, if the CT value is 130-199, the calcification density score is 1 score; if the CT value is 200-299, the calcification density score is 2 scores; if the CT value is 300-399, the calcification density score is 3 scores; if the CT value is greater than 400, the calcification density score is 4 scores. Then, the calcification Agatston score of the calcification sub-region is obtained by multiplying the calcification density score of the calcification sub-region by the calcification area of the calcification sub-region. Finally, a total calcification Agatston score of the entire coronary region is obtained by calculating a sum of the calcification Agatston scores of all calcification sub-regions in the coronary region. The calcification score is calculated by the volume score method based on the following principle: the number of pixel points in the calcification region is multiplied by a physical unit of the pixel point (e.g., the physical unit is mm$^3$). For example, for each calcification sub-region in the coronary region, the number of pixel points included in the calcification sub-region is calculated and then multiplied by the physical unit of the pixel point, so as to obtain the volume score of the calcification sub-region. Finally, a total calcification volume score of the entire coronary region may be obtained by calculating a sum of the volume scores of all calcification sub-regions in the coronary region. The quality score method is used to further correct the volume score method. The quality score=volume score×correction factor×mean gray level, where the correction factor is calculated according to a known calcium density $\rho_{HA}$, a mean CT value of water $\overline{CT}_{water}$ and a mean CT value of calcium $\overline{CT}_{HA}$ in the following formula:

$$c_{HA} = \frac{\rho_{HA}}{\overline{CT}_{HA} - \overline{CT}_{water}}.$$

For example, for each calcification sub-region in the coronary region, the quality score of the calcification sub-region may be calculated according to the volume score and the mean gray level of the calcification sub-region in the above quality score formula. Finally, a total calcification quality score of the entire coronary region may be obtained by calculating a sum of the quality scores of all calcification sub-regions in the coronary region.

In an example, displaying the score value may include: displaying respective calcification scores of various calcification sub-regions in the coronary region. The calcification score includes a calcification Agatston score, a calcification volume score and a calcification quality score.

Figure 2:
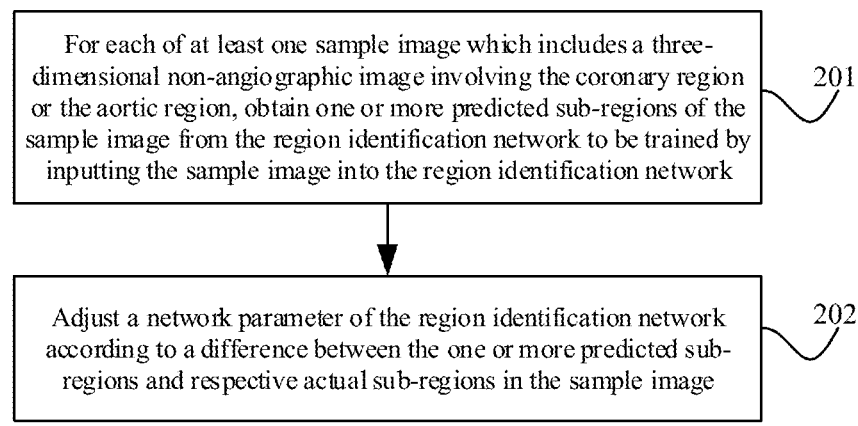
FIG. 2 is a flowchart of training of a region identification network according to one or more embodiments of the present disclosure.

Before step 102 is performed, the region identification network to be used in step 102 can be pre-trained, so as to identify different to-be-detected sub-regions included in a to-be-detected region in the three-dimensional non-angiographic image. FIG. 2 is a flowchart of a process of training a region identification network according to an example of the present disclosure. As shown in FIG. 2, the process may include steps 201-202.

At step 201, for each of at least one sample image which includes a three-dimensional non-angiographic image involving the coronary region or the aortic region, one or more predicted sub-regions of the sample image from the region identification network to be trained is obtained by inputting the sample image into the region identification network.

A large number of sample images are to be used as training data so as to obtain a region identification network satisfying a use condition through a deep neural network. For example, a large number of three-dimensional non-angiographic images involving the coronary region and the aortic region are input as training data into the to-be-trained region identification network. The region identification network analyzes and predicts the coronary region, the aortic region and respective to-be-detected sub-regions in the coronary region and the aortic region according to the three-dimensional non-angiographic images. For example, the region identification network predicts a plurality of to-be-detected sub-regions in the coronary region: a left main coronary artery region, a left anterior descending artery region, a circumflex artery region, and a right coronary artery region; and predicts a plurality of to-be-detected sub-regions in the aortic region: an aortic valve region, an ascending aorta region, a aortic arch region, and a descending aorta region.

At step 202, a network parameter of the region identification network is adjusted according to a difference between the one or more predicted sub-regions and respective actual sub-regions in the sample image.

For example, difference comparison is performed between a plurality of predicted to-be-detected sub-regions in the coronary region: the predicted left main coronary artery region, the predicted left anterior descending artery region, the predicted circumflex artery region and the predicted right coronary artery region and a plurality of actual to-be-detected sub-regions within the coronary region in the sample image: the actual left main coronary artery region, the actual left anterior descending artery region, the actual circumflex artery region and the actual right coronary artery region, and then the network parameter of the region identification network is adjusted according to the difference. The network parameter of the region identification network is adjusted through several iterative trainings with a large number of sample images as training data, so that a region identification network having an identification capability is obtained finally.

Descriptions are made below with a three-dimensional non-angiographic image involving the coronary region as training data, where the to-be-detected sub-regions in the coronary region include the left main coronary artery region, the left anterior descending artery region, the circumflex artery region, and the right coronary artery region. Firstly, by the combination of VGG model, down-sampling and up-sampling, the deep neural network is designed as the to-be-trained region identification network, where the manner in which the deep neural network is designed is not limited in the present disclosure. Next, a large number of three-dimensional non-angiographic images involving the coronary region are input into the region identification network, where the to-be-detected sub-regions in the coronary region are marked in the three-dimensional non-angiographic images so that different markers correspond to different coronary types, for example, the left main coronary artery region is marked with 1, the left anterior descending artery region is marked with 2, the circumflex artery region is marked with 3, and the right coronary artery region is marked with 4. The region identification network analyzes and predicts to-be-detected sub-regions in the coronary region according to the input three-dimensional non-angiographic images involving the coronary region. The region identification network adjusts the network parameter of the region identification network by performing difference comparison between the one or more predicted to-be-detected sub-regions and respective actual to-be-detected sub-regions in the three-dimensional non-angiographic image. Finally, a region identification network having an identification capability is obtained through training iterations of a large number of sample images.

Figure 4:
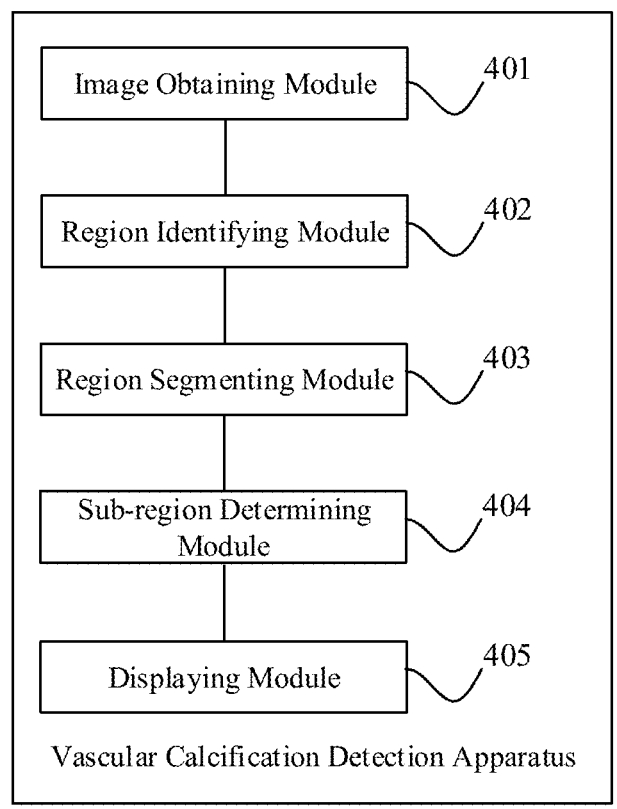
FIG. 4 is a schematic diagram of an apparatus of detecting vascular calcification according to one or more embodiments of the present disclosure.

As shown in FIG. 4, implementations of the present disclosure also provide an apparatus of detecting vascular calcification which may perform the method of detecting vascular calcification according to any one example of the present disclosure. The apparatus may include an image obtaining module 401, a region identifying module 402, a region segmenting module 403, a sub-region determining module 404, and a displaying module 405. The image obtaining module 401 is configured to obtain a three-dimensional non-angiographic image; the region identifying module 402 is configured to obtain one or more to-be-detected sub-regions included in each of at least two to-be-detected regions in the three-dimensional non-angiographic image by inputting the three-dimensional non-angiographic image into a pre-trained region identification network, where the to-be-detected regions involve an aortic region and a coronary region; the region segmenting module 403 is configured to, for each of the to-be-detected regions, obtain a calcification region in the to-be-detected region by a threshold segmentation method; the sub-region determining module 404 is configured to determine a calcification sub-region in each of the one or more to-be-detected sub-regions included in the to-be-detected region based on the calcification region and the one or more to-be-detected sub-regions included in the to-be-detected region; and the displaying module 405 is configured to display the calcification sub-region in each of the one or more to-be-detected sub-regions in the three-dimensional non-angiographic image.

Figure 5:
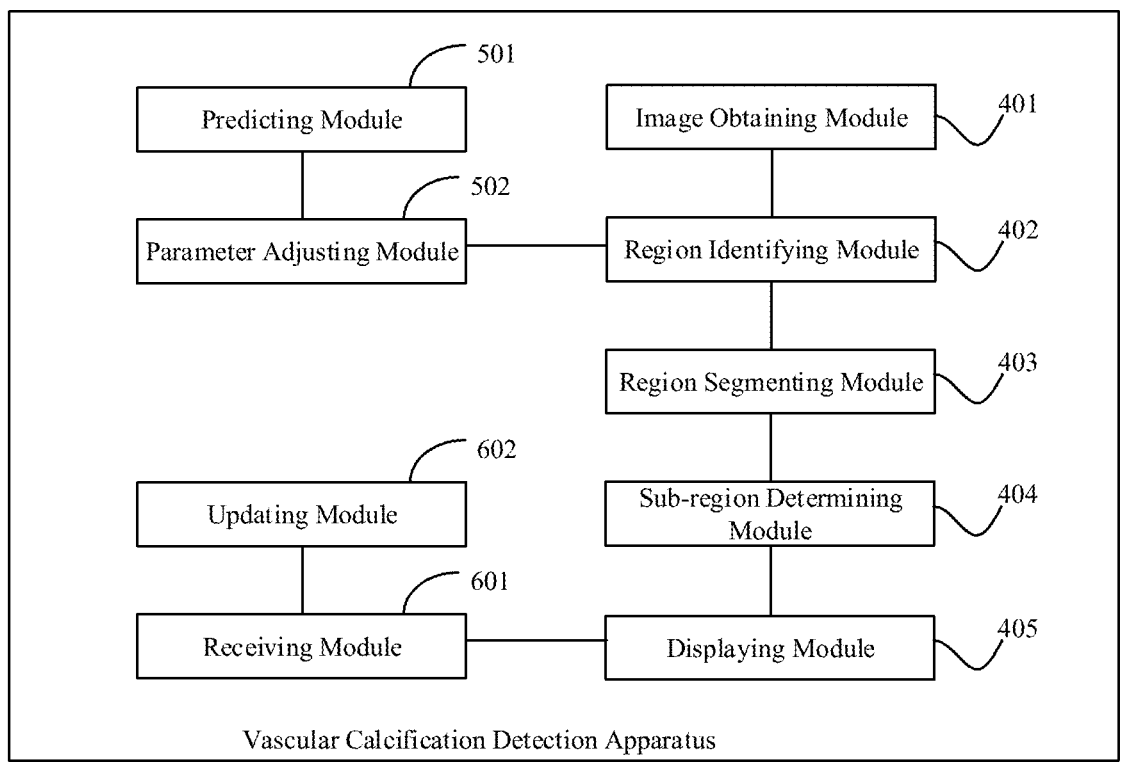
FIG. 5 is a schematic diagram of another apparatus of detecting vascular calcification according to one or more embodiments of the present disclosure.

Optionally, as shown in FIG. 5, the apparatus can further include: a predicting module 501 configured to, for each of at least one sample image which includes a three-dimensional non-angiographic image involving the coronary region or the aortic region, obtain one or more predicted sub-regions of the sample image from the region identification network to be trained by inputting the sample image into the region identification network; and a parameter adjusting module 502 configured to adjust a network parameter of the region identification network according to a difference between the one or more predicted sub-regions and respective actual sub-regions in the sample image.

Optionally, the region segmenting module 403 is configured to: mark a region with a CT value greater than or equal to a preset threshold within the aortic region in the to-be-detected region as a suspicious aortic calcification region; obtain an aortic calcification region by removing a non-calcification region within the suspicious aortic calcification region according to a first preset condition.

Optionally, the first preset condition includes preset regional connectivity and regional volume.

Optionally, the region segmenting module 403 is configured to: mark a region with a CT value greater than or equal to a preset threshold within the coronary region in the to-be-detected region as a suspicious coronary calcification region; obtain a coronary calcification region by removing a non-calcification region within the suspicious coronary calcification region according to a second preset condition.

Optionally, the second preset condition includes preset regional morphology and regional space feature.

Optionally, as shown in FIG. 5, the apparatus further includes: a receiving module 601, configured to receive a parameter modification request, where the parameter modification request includes data for updating the calcification sub-region; and an updating module 602 configured to update the calcification sub-region according to the parameter modification request.

Optionally, the displaying module 405 is further configured to: calculate a score value of the calcification sub-region, where the score value represents a calcification degree of the calcification sub-region; and display the score value.

Details of the implementation process of the functions and effects of different modules in the above-described apparatus may be seen from the implementation process of corresponding steps in the above-described method, which will not be redundantly described herein.

Since the apparatus examples substantially correspond to the method examples, a reference may be made to part of the descriptions of the method examples for the related part. The apparatus examples described above are merely illustrative, where the units described as separate members may be or not be physically separated, and the members displayed as units may be or not be physical units, i.e., may be located in one place, or may be distributed to a plurality of network units. Part or all of the modules may be selected according to actual requirements to implement the objectives of the solutions in the examples. Those of ordinary skill in the art may understand and carry out them without creative work.

The present disclosure further provides a computer device including a memory, a processor and a computer program stored on the memory and run on the processor. The processor executes the computer program to implement the method of detecting vascular calcification in any one example of the present disclosure.

The present disclosure further provides a non-transitory computer readable storage medium storing a computer program. The computer program is executed by a processor to implement the method of detecting vascular calcification in any one example of the present disclosure.

The non-transitory computer readable storage medium may be a Read-Only Memory (ROM), a Random Access Memory (RAM), a CD-ROM, a magnetic tape, a floppy disk, an optical data storage device, and so on, which is not limited herein.

Other implementations of the present disclosure will be apparent to those skilled in the art from consideration of the specification and practice of the present disclosure herein. The present disclosure is intended to cover any variations, uses, modification or adaptations of the present disclosure that follow the general principles thereof and include common knowledge or conventional technical means in the related art that are not disclosed in the present disclosure. The specification and examples are considered as exemplary only, with a true scope and spirit of the present disclosure being indicated by the following claims.

It is to be understood that the present disclosure is not limited to the precise structure described above and shown in the accompanying drawings, and that various modifications and changes may be made without departing from the scope thereof. The scope of the present disclosure is limited only by the appended claims.

The foregoing disclosure is merely illustrative of preferred examples of the present disclosure but not intended to limit the present disclosure, and any modifications, equivalent substitutions, adaptations thereof made within the spirit and principles of the disclosure shall be encompassed in the scope of protection of the present disclosure.

The invention claimed is:

1. A method of detecting vascular calcification, the method comprising:
   obtaining a three-dimensional non-angiographic image;
   obtaining one or more to-be-detected sub-regions included in each of at least two to-be-detected regions in the three-dimensional non-angiographic image by inputting the three-dimensional non-angiographic image into a pre-trained region identification network, wherein the at least two to-be-detected regions include an aortic region and a coronary region;
   for each of the at least two to-be-detected regions,
      obtaining a calcification region in the to-be-detected region by threshold segmentation;
      determining, based on the calcification region and the one or more to-be-detected sub-regions included in the to-be-detected region, a corresponding calcification sub-region in each of the one or more to-be-detected sub-regions included in the to-be-detected region; and
      displaying, in the three-dimensional non-angiographic image, the corresponding calcification sub-region in each of the one or more to-be-detected sub-regions.

2. The method according to claim 1, wherein the region identification network is pre-trained by:
   for each of at least one sample image that includes a three-dimensional non-angiographic image involving the coronary region or the aortic region,
      obtaining one or more predicted sub-regions of the sample image from the region identification network by inputting the sample image into the region identification network; and
      adjusting a network parameter of the region identification network according to a difference between the obtained one or more predicted sub-regions and one or more corresponding actual sub-regions in the sample image.

3. The method according to claim 1, wherein obtaining the calcification region in the to-be-detected region by the threshold segmentation comprises:
   marking a region with a CT value greater than or equal to a preset threshold within the aortic region in the to-be-detected region as a suspicious aortic calcification region; and
   obtaining an aortic calcification region by removing a non-calcification region within the suspicious aortic calcification region according to a first preset condition.

4. The method according to claim 3, wherein the first preset condition comprises preset regional connectivity and regional volume.

5. The method according to claim 1, wherein obtaining the calcification region in the to-be-detected region by the threshold segmentation comprises:
   marking a region with a CT value greater than or equal to a preset threshold within the coronary region in the to-be-detected region as a suspicious coronary calcification region; and
   obtaining a coronary calcification region by removing a non-calcification region within the suspicious coronary calcification region according to a second preset condition.

6. The method according to claim 5, wherein the second preset condition comprises preset regional morphology and regional space feature.

7. The method according to claim 1, wherein, after displaying the calcification sub-region, the method further comprises:
   receiving a parameter modification request, wherein the parameter modification request comprises data for updating the calcification sub-region; and
   updating the corresponding calcification sub-region according to the parameter modification request.

8. The method according to claim 1, wherein, after displaying the calcification sub-region, the method further comprises:
   calculating a score value of the corresponding calcification sub-region, wherein the score value represents a calcification degree of the corresponding calcification sub-region; and
   displaying the score value of the corresponding calcification sub-region.

9. A computer device comprising:
   at least one processor; and
   at least one non-transitory machine readable storage medium coupled to the at least one processor having machine-executable instructions stored thereon that, when executed by the at least one processor, cause the at least one processor to perform operations comprising:
      obtaining a three-dimensional non-angiographic image;
      obtaining one or more to-be-detected sub-regions included in each of at least two to-be-detected regions in the three-dimensional non-angiographic image by inputting the three-dimensional non-angiographic image into a pre-trained region identification network, wherein the at least two to-be-detected regions include an aortic region and a coronary region;
      for each of the at least two to-be-detected regions,
         obtaining a calcification region in the to-be-detected region by threshold segmentation;
         determining, based on the calcification region and the one or more to-be-detected sub-regions included in the to-be-detected region, a corresponding calcification sub-region in each of the one or more to-be-detected sub-regions included in the to-be-detected region; and
         displaying, in the three-dimensional non-angiographic image, the corresponding calcification sub-region in each of the one or more to-be-detected sub-regions.

10. The device according to claim 9, wherein the operations further comprise pre-training the region identification network by:
for each of at least one sample image that includes a three-dimensional non-angiographic image involving the coronary region or the aortic region,
obtaining one or more predicted sub-regions of the sample image from the region identification network by inputting the sample image into the region identification network; and
adjusting a network parameter of the region identification network according to a difference between the obtained one or more predicted sub-regions and one or more corresponding actual sub-regions in the sample image.

11. The device according to claim 9, wherein obtaining the calcification region in the to-be-detected region by the threshold segmentation comprises:
marking a region with a CT value greater than or equal to a preset threshold within the aortic region in the to-be-detected region as a suspicious aortic calcification region; and
obtaining an aortic calcification region by removing a non-calcification region within the suspicious aortic calcification region according to a first preset condition.

12. The device according to claim 11, wherein the first preset condition comprises preset regional connectivity and regional volume.

13. The device according to claim 9, wherein obtaining the calcification region in the to-be-detected region by the threshold segmentation comprises:
marking a region with a CT value greater than or equal to a preset threshold within the coronary region in the to-be-detected region as a suspicious coronary calcification region; and
obtaining a coronary calcification region by removing a non-calcification region within the suspicious coronary calcification region according to a second preset condition.

14. The device according to claim 13, wherein the second preset condition comprises preset regional morphology and regional space feature.

15. The device according to claim 9, wherein the operations further comprise:
receiving a parameter modification request, wherein the parameter modification request comprises data for updating the calcification sub-region; and
updating the corresponding calcification sub-region according to the parameter modification request.

16. The device according to claim 9, wherein the operations further comprise:
calculating a score value of the corresponding calcification sub-region, wherein the score value represents a calcification degree of the corresponding calcification sub-region; and
displaying the score value of the corresponding calcification sub-region.

17. A non-transitory computer-readable storage medium coupled to at least one processor and storing programming instructions for execution by the at least one processor, wherein the programming instructions instruct the at least one processor to perform operations comprising:
obtaining a three-dimensional non-angiographic image;
obtaining one or more to-be-detected sub-regions included in each of at least two to-be-detected regions in the three-dimensional non-angiographic image by inputting the three-dimensional non-angiographic image into a pre-trained region identification network, wherein the at least two to-be-detected regions include an aortic region and a coronary region;
for each of the at least two to-be-detected regions,
obtaining a calcification region in the to-be-detected region by threshold segmentation;
determining, based on the calcification region and the one or more to-be-detected sub-regions comprised in the to-be-detected region, a corresponding calcification sub-region in each of the one or more to-be-detected sub-regions included in the to-be-detected region; and
displaying, in the three-dimensional non-angiographic image, the corresponding calcification sub-region in each of the one or more to-be-detected sub-regions.

18. The non-transitory computer-readable storage medium according to claim 17, wherein the operations further comprise pre-training the region identification network by:
for each of at least one sample image that includes a three-dimensional non-angiographic image involving the coronary region or the aortic region,
obtaining one or more predicted sub-regions of the sample image from the region identification network by inputting the sample image into the region identification network; and
adjusting a network parameter of the region identification network according to a difference between the obtained one or more predicted sub-regions and one or more corresponding actual sub-regions in the sample image.

19. The non-transitory computer-readable storage medium according to claim 17, wherein obtaining the calcification region in the to-be-detected region by the threshold segmentation comprises:
marking a region with a CT value greater than or equal to a preset threshold within the aortic region in the to-be-detected region as a suspicious aortic calcification region; and
obtaining an aortic calcification region by removing a non-calcification region within the suspicious aortic calcification region according to a first preset condition.

20. The non-transitory computer-readable storage medium according to claim 17, wherein obtaining the calcification region in the to-be-detected region by the threshold segmentation comprises:
marking a region with a CT value greater than or equal to a preset threshold within the coronary region in the to-be-detected region as a suspicious coronary calcification region; and
obtaining a coronary calcification region by removing a non-calcification region within the suspicious coronary calcification region according to a second preset condition.

* * * * *